(12) United States Patent
Kim (10) Patent No.: US 11,562,817 B2
(45) Date of Patent: Jan. 24, 2023

(54) MEAL SERVICE MANAGEMENT SYSTEM AND OPERATING METHOD THEREFOR

(71) Applicant: NUVI LABS CO., LTD., Suwon-si (KR)

(72) Inventor: Dae Hoon Kim, Gunpo-si (KR)

(73) Assignee: NUVI LABS CO., LTD., Suwon-si (KR)

( * ) Notice: Subject to any disclaimer, the term of this patent is extended or adjusted under 35 U.S.C. 154(b) by 18 days.

(21) Appl. No.: 16/763,920

(22) PCT Filed: Nov. 8, 2018

(86) PCT No.: PCT/KR2018/013529
§ 371 (c)(1),
(2) Date: May 13, 2020

(87) PCT Pub. No.: WO2019/098600
PCT Pub. Date: May 23, 2019

(65) Prior Publication Data
US 2020/0365250 A1 Nov. 19, 2020

(30) Foreign Application Priority Data
Nov. 14, 2017 (KR) .......................... 10-2017-0151469

(51) Int. Cl.
*G16H 20/60* (2018.01)
*G06T 7/62* (2017.01)
(Continued)

(52) U.S. Cl.
CPC .............. *G16H 20/60* (2018.01); *G01K 13/00* (2013.01); *G06F 16/23* (2019.01); *G06K 7/1413* (2013.01);
(Continued)

(58) Field of Classification Search
CPC .......... G16H 20/60; G16H 40/67; G06T 7/62; G06T 7/97; G06H 40/67; G06H 50/30; G06Q 30/0269; G06Q 30/0206
See application file for complete search history.

(56) References Cited

U.S. PATENT DOCUMENTS 8,363,913 B2    1/2013  Boushey et al.
9,424,495 B1 *  8/2016  Trevino ............... A61B 5/4866
(Continued)

FOREIGN PATENT DOCUMENTS

CN    105320955 A        2/2016
CN    110455389 A   *   11/2019
(Continued)

OTHER PUBLICATIONS

AU Office Action in Application No. 2018370069 dated Mar. 26, 2021.
(Continued)

*Primary Examiner* — Scott C Anderson
(74) *Attorney, Agent, or Firm* — Maschoff Brennan (57) ABSTRACT

The present invention relates to a meal service management system and an operating method therefor, the system being capable of providing information on food ingested by a user to whom a meal service is to be provided and customized information related thereto, and managing food leftover in a meal service. According to an embodiment of the present invention, a scanner device is used such that a user to whom a meal service is to be provided and a food tray before and after meals are identified, and thus a meal service amount and a leftovers food amount are acquired, and leftovers food information of each user and useful information associated therewith are provided on the basis of the same, and thus users can easily determine their eating habits, nutritional (Continued)

status and the like and the users can be induced to attempt reducing leftovers food by themselves.

11 Claims, 8 Drawing Sheets (51) Int. Cl.
| | |
|---|---|
| *G06T 7/00* | (2017.01) |
| *G16H 40/67* | (2018.01) |
| *G16H 50/30* | (2018.01) |
| *G06F 16/23* | (2019.01) |
| *G01K 13/00* | (2021.01) |
| *G06K 7/14* | (2006.01) |
| *G06Q 30/00* | (2012.01) |
| *G06Q 30/02* | (2012.01) |
| *G06Q 40/08* | (2012.01) |
| *G06Q 50/12* | (2012.01) |

(52) U.S. Cl.
CPC ....... *G06K 7/1417* (2013.01); *G06Q 30/0185* (2013.01); *G06Q 30/0206* (2013.01); *G06Q 30/0269* (2013.01); *G06Q 40/08* (2013.01); *G06Q 50/12* (2013.01); *G06T 7/62* (2017.01); *G06T 7/97* (2017.01); *G16H 40/67* (2018.01); *G16H 50/30* (2018.01)

(56) References Cited

U.S. PATENT DOCUMENTS

| | | | |
|---|---|---|---|
| 2002/0095343 A1 | 7/2002 | Barton et al. | |
| 2008/0077455 A1* | 3/2008 | Gilboa | G06Q 50/00 |
| | | | 705/5 |
| 2013/0218511 A1* | 8/2013 | Mager | G16H 20/60 |
| | | | 702/129 |
| 2014/0315162 A1 | 10/2014 | Ehrenkranz | |
| 2015/0228062 A1 | 8/2015 | Joshi et al. | |
| 2015/0228082 A1 | 8/2015 | Wheeler et al. | |
| 2015/0363860 A1* | 12/2015 | Lantrip | G06Q 30/0631 |
| | | | 705/5 |
| 2016/0098942 A1* | 4/2016 | Messier | G09B 19/0092 |
| | | | 434/127 |
| 2017/0020461 A1* | 1/2017 | Quinn | A61B 5/11 |
| 2017/0184383 A1* | 6/2017 | Lee | H04N 5/247 |
| 2017/0278203 A1* | 9/2017 | Mimassi | G06Q 50/12 |
| 2017/0365017 A1* | 12/2017 | Ells | G06Q 20/208 |

FOREIGN PATENT DOCUMENTS

| | | |
|---|---|---|
| EP | 3070694 A1 | 9/2016 |
| JP | 10-069579 A | 1/1994 |
| JP | 2004-127219 A | 4/2004 |
| JP | 2005-250885 A | 9/2005 |
| JP | 2014-164411 A | 9/2014 |
| JP | 2018-147415 A | 9/2018 |
| KR | 10-0975960 B1 | 8/2010 |
| KR | 10-2012-0588294 A | 6/2012 |
| KR | 10-2014-0087870 A | 7/2014 |
| KR | 20140094761 A | 7/2014 |
| KR | 10-2017-0014181 A | 2/2017 |
| RU | 2266561 C2 | 12/2005 |
| WO | 2017/044161 A1 | 3/2017 |

OTHER PUBLICATIONS

JP Office Action in Application No. 2020-545028 dated May 18, 2021.

RU Office Action in Application No. 2020119569 dated Dec. 23, 2020.

McClung et al., "Digitial food photography technology improves efficiency and feasibility of dietary intake assessments in large populations eating ad libitum in collective dining facilities", Appetite 116 (2017) 389-394, May 17, 2017.

European Search Report issued in corresponding application No. 18879473, dated Jul. 20, 2021.

JP Office Action in Application No. 2020-545028 dated Mar. 1, 2022.

* cited by examiner

MEAL SERVICE MANAGEMENT SYSTEM AND OPERATING METHOD THEREFOR

TECHNICAL FIELD

The present invention relates to a meal service management system, and more particularly, to a meal service management system and an operating method therefor, the system being capable of providing information on food ingested by a user who is a meal service recipient and customized information related thereto and of managing leftovers in a meal service.

BACKGROUND ART

Currently, students, office workers, or other meal service recipients who are served meals at school cafeterias, company cafeterias, and other cafeterias often have one or more meals a day at the same establishment. In particular, students eat lunch at school cafeterias during most of the week, excluding the weekend, and it is important to provide these growing students with an environment in which they can eat nutritious meals.

However, children in early elementary school are unfamiliar with eating a meal as much as they need and often tend to eat only what they like without eating a balanced diet, but there is no way to check whether the children are eating a balanced diet. This is the same for late elementary school students.

In particular, parents with elementary school children have a great desire to manage their children's diet, and are struggling with ways to improve their children's eating habits, such as the rate and amount of food intake and the habit of not leaving leftovers.

In addition, office workers who frequently use company cafeterias also desire to check and manage their eating habits, and it is necessary for nurses of hospitals providing a meal service system to accurately know the amount of food intake of patients. However, there is currently no service that is capable of providing eating habit information based on accurate data.

DISCLOSURE

Technical Problem

Therefore, the present invention has been made in view of the above problems, and it is an object of the present invention to provide a meal service recipient of cafeterias at schools, companies, and hospitals, for example, with ingestion information and other useful information related thereto based on the amount of leftovers.

Technical Solution

To solve the object described above, in accordance with one embodiment of the present invention, provided is a meal service management system including a first scanner configured to scan an ID card of a user who is a meal service recipient to identify the user, a second scanner configured to scan a tray identifier code to identify a tray, and acquire a pre-meal image of the tray before a meal of the user, a third scanner configured to scan the identified tray after the meal to acquire a post-meal image of the tray of the user, and a management server configured to control the first to third scanners to generate ingestion information of the user based on an acquired pre-meal and post-meal images.

The management server may include a user management unit configured to register the user as a meal service recipient, and provide nutritional information including one of eating habits and nutritive conditions of registered users, a cafeteria management unit configured to register a cafeteria, and provide operating information related to an operation of the registered cafeteria, a device control unit connected to the first to third scanners to receive acquired scanning data, an image processor configured to generate the ingestion information based on the scanning data received by the device control unit, and a database configured to store personal information of the user and the operating information of the cafeteria.

The user management unit may include a personal information processing module configured to generate, update, or delete the personal information of the user, an eating habit determination module configured to determine an eating habit of the user based on ingestion information for a predetermined duration and apply the eating habit to the nutritional information, and a nutritive condition estimation module configured to estimate a current nutritive condition of the user according to the nutritional information.

The cafeteria management unit may include a cafeteria management module configured to generate, update, or delete the operating information, a food material examination module configured to generate examination information based on an examination result of a nutritionist with respect to a plurality of food materials supplied to the cafeteria, and a menu generation module configured to generate a menu list in response to an input of the nutritionist.

The image processor may include a pre-processing module configured to pre-process the post-meal image obtained by photographing the tray after the meal, a comparison module configured to compare the post-meal image with the pre-meal image received from an image storage, a leftovers estimation module configured to generate leftovers information based on a comparison result of the comparison module, and an ingestion information generation module configured to generate the ingestion information based on the leftovers information and output the ingestion information as a numerical value, text, or a graph.

The third scanner may further be connected to at least one sensor, and the image processor may further include a correction module configured to receive a sensing value from the sensor and generate a correction value for correction of the leftovers information based on the sensing value.

The management server may include an advertisement management unit configured to provide advertisement information for a medical appliance or food customized for each user, recommended menu information, or other additional information with reference to the nutritional information.

Each of the second and third scanners may include a body, a support connected perpendicularly to one side of the body, a cradle coupled to a top of the support, the tray being seated on the cradle, and a camera provided on the one side of the body so as to face a top of the cradle and configured to photograph food on the tray.

A bottom of the cradle may be supported by and coupled to at least one load cell provided on the support.

The cradle may be equipped with at least one temperature sensor that senses a temperature of the tray seated on the top of the cradle.

The management server may include a meal cost management unit configured to differentially calculate a meal cost for an amount of food per person depending on ingestion information for each user.

The management server may be linked to at least one external system that provides an insurance service, a user monitoring service, or a medical service via an information communication network.

Further, in accordance with an embodiment of another aspect of the present invention to solve the object described above, provided is an operating method of a meal service management system including identifying a user who is a meal service recipient by scanning a user ID card, identifying a tray before a meal by scanning a tray identifier code and acquiring a pre-meal image of the tray of the user, acquiring a post-meal image of the identified tray of the user by scanning the tray after the meal, and calculating leftovers information based on an acquired pre-meal and post-meal images and generating ingestion information corresponding to the leftovers information.

The operating method may further include, after the generating the ingestion information, displaying the ingestion information depending on the meal and outputting a coupon according to the ingestion information.

Advantageous Effects

As apparent from the foregoing, according to an embodiment of the present invention, the amount of food served and the amount of leftovers may be acquired by identifying a user who is a meal service recipient and a tray before and after a meal using scanner devices, and based on an acquired information, ingestion information of respective users and other useful information related thereto may be provided. This may allow the users to easily check their eating habits and nutritive conditions, for example, and may induce the users to try to leave less leftovers.

Further, according to the embodiment of the present invention, for example, cafeteria managers and nutritionists as well as meal service recipients may grasp preferred foods and eating behavior of respective meal service recipients as well as nutrition ingestion information by utilizing leftovers information acquired via a meal service management system and may apply the grasped result to a meal service, which may improve the quality of a meal and may cause a reduction in the amount of leftovers.

BEST MODE

Prior to the description, when an element is referred to as "having" or "including" another element throughout the specification, this means that the element may further include other elements, rather than excluding other elements, so long as there is no special conflicting description. In addition, terms such as, for example, "module" and "unit" described herein imply a basic unit of processing at least one function or operation, and may be implemented in hardware, software, or a combination of hardware and software.

Further, "embodiment" herein means to serve as an example, a case, or an illustration, but an object of the present invention is not limited thereby. Furthermore, other similar terms such as, for example, "including", "having", and "with" are used, but when used in the claims, are comprehensively used similarly to the term "comprising" as an open transition word that does not exclude any additional or other components.

Various techniques described herein may be implemented with hardware or software, or may be implemented with a combination of hardware and software where appropriate. As used herein, terms such as, for example, "unit", "module" and "system" may likewise be treated as being equivalent to computer related entities, i.e., hardware, software, a combination of hardware and software, or software at the time of execution. For example, a program module may be equivalent to one component, or may be composed of a combination of two or more components. In addition, in the present invention, both hardware and an application program executed in a server or a terminal may be configured in the form of a module, may be recorded on one physical memory, or may be distributed between and recorded on two or more memories and recording media.

Hereinafter, a meal service management system and an operating method therefor according to an exemplary embodiment of the present invention will be described with reference to the drawings.

Figure 1:
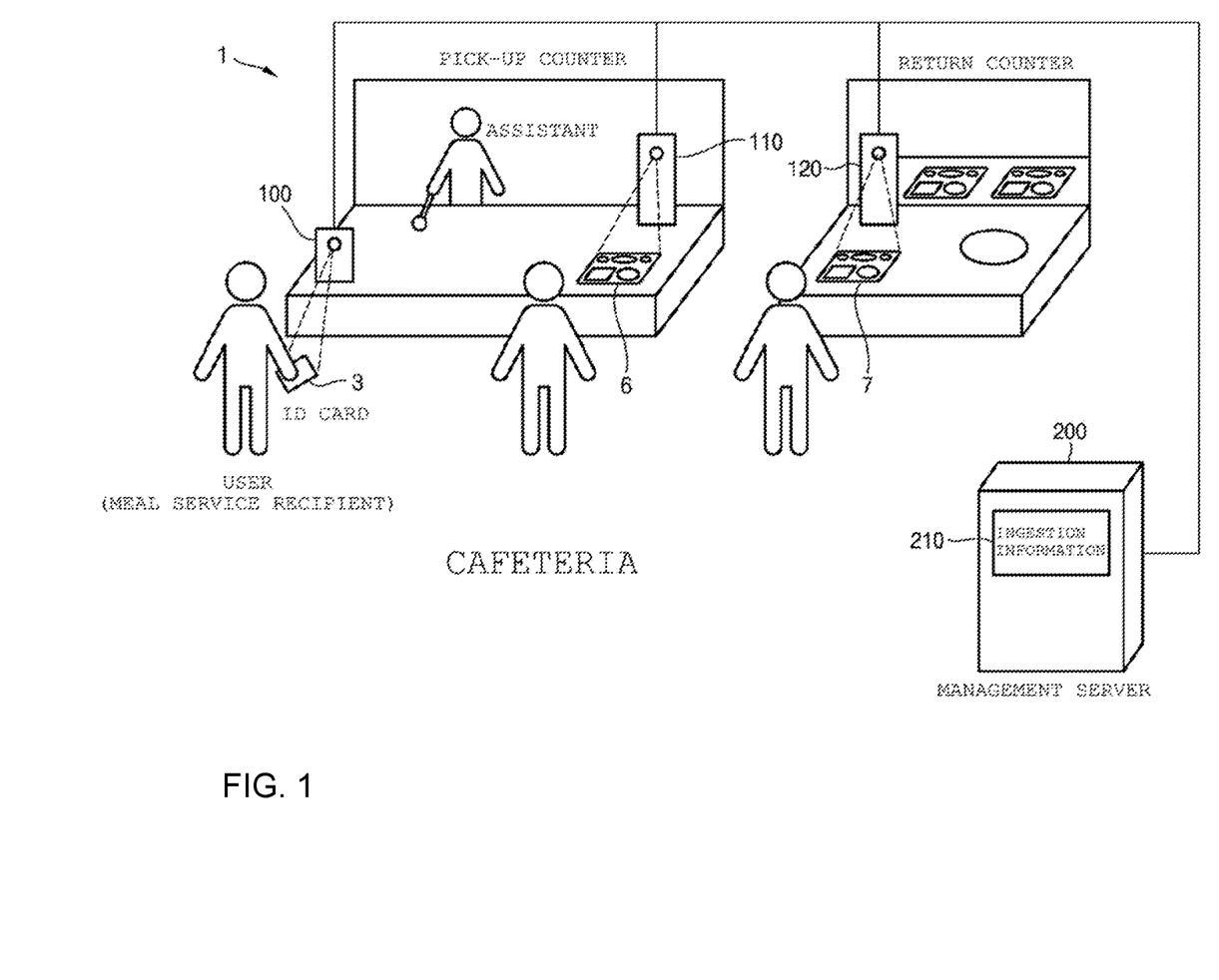
FIG. 1 is a diagram schematically illustrating the configuration of a cafeteria to which a meal service management system according to an embodiment of the present invention is applied.

FIG. 1 is a diagram schematically illustrating the configuration of a cafeteria to which a meal service management system according to an embodiment of the present invention is applied.

Referring to FIG. 1, the meal service management system according to the embodiment of the present invention may include a first scanner 100 which scans an ID card of a user who is a meal service recipient to identify the user, a second scanner 110 which scans a tray identifier code to identify a tray and acquire a pre-meal image of the tray before a meal of the user, a third scanner 120 which scans the identified tray after the meal to acquire a post-meal image of the tray of the user, and a management server 200 which controls the first to third scanners to generate ingestion information based on an acquired pre-meal and post-meal images.

The meal service management system according to the embodiment of the present invention may be provided at a predetermined cafeteria 1 that serves meals to a large number of students at a school, and may include multiple scanning devices and the management server 200 connected thereto, the management server having a display unit.

The first scanner 100 serves to identify a meal service recipient, and to this end, scans an ID card possessed by a user and transmits the scanning result to the management server 200 so that the management server 200 may determine whether or not the user is a meal service recipient with reference to personal information stored therein. Here, the ID card may be a student ID card, a name tag, or an employee ID card. According to the intention of a designer, a method of identifying a user through a facial recognition technique of photographing the face of the user via a camera, rather than using the ID card, may also be applied.

Here, a vision recognition technique may be applied to the meal service management system to enhance the accuracy of user identification. In this case, the meal service management system may be linked to a school or company attendance system so that a user is photographed every day when the user arrives at school or work, and may store the photographed result in a database and then utilize the same to identify the user for the progress of a meal service by applying the vision recognition technique to the face, shoes, cloths, or hair style of the user, for example.

Alternatively, a method of identifying a user via communication with a portable terminal carried by the user without scanning may be used.

The second scanner 110 may scan a tray 6 before a meal, which contains food thereon, at a pick-up counter and may transmit an image of the tray to the management server 200. Here, the second scanner also scans an identifier code on the tray 6 and transmits the identifier code to the management server. Thereby, the management server 200 may distinguish trays from each other, and may determine the amount of food on each tray, i.e., the amount of food served to each user. The identifier code may be implemented as a barcode or a QR code, for example.

The third scanner 120 may scan a tray 7 after a meal, which contains leftovers, before the user processes the leftovers at a return counter and may provide an image of the tray to the management server 200. Here, the third scanner also scans the identifier code on the tray 7 and transmits the identifier code to the management server. Thereby, the management server 200 may determine the user of the tray 7 and the amount of leftovers for each user. Thereafter, the management server 200 may calculate leftovers information based on the amount of food served and the amount of leftovers and consequently, generate ingestion information.

The management server 200 may be provided in one side of the cafeteria 1, preferably near the exit of the cafeteria 1, and may display ingestion information for each user on a display unit 210 mounted therein.

The management server 200 may be connected to the respective scanners 100 to 130 via a network, and may generate and provide user information and user ingestion information based on the results transmitted from the scanners 100 to 130, such as the ID card scanning result, the tray identifying result, and the pre-meal and post-meal images of the tray.

In particular, in the meal service management system according to the embodiment of the present invention, ingestion information for each user may be quantified by applying an image processing technique to images acquired via the scanners, and may be provided as a numerical value, text, or a graph, for example. A detailed description related to components of the management server 200 will be given below.

According to the above-described configuration, the meal service management system according to the embodiment of the present invention may be provided at a cafeteria, and may identify a user, acquire the amount of food served and the amount of leftovers using scanned pre-meal and post-meal images of a tray, and generate and provide ingestion information of the user and other various nutritional information based on an acquired results, thereby allowing the user to easily check their eating habits.

Hereinafter, the management server included in the meal service management system according to the embodiment of the present invention will be described with reference to the drawings.

Figure 2A:
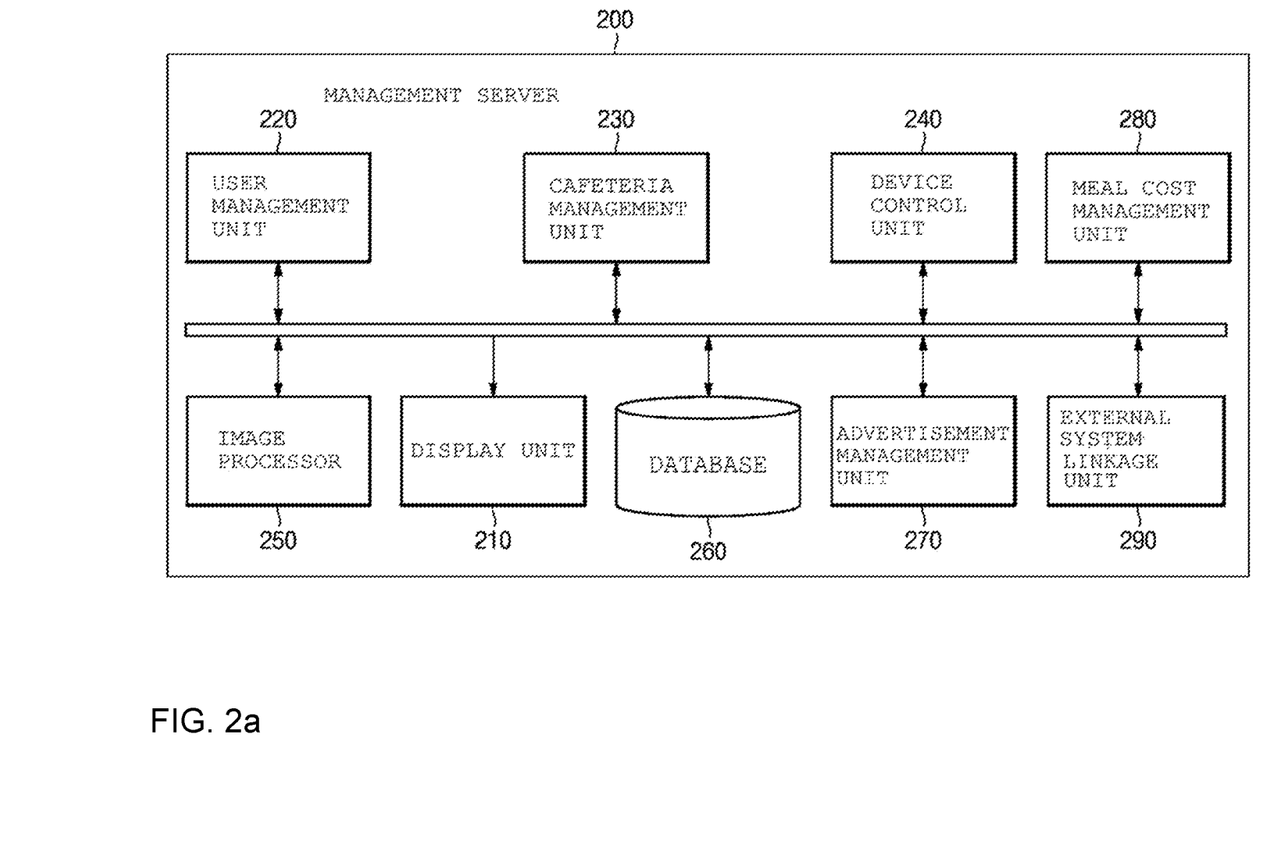
FIG. 2a is a diagram illustrating the configuration of a management server of the meal service management system according to the embodiment of the present invention.

FIG. 2a is a diagram illustrating the configuration of the management server of the meal service management system according to the embodiment of the present invention. In the following description, respective components constituting the management server of the present invention may be implemented in the form of a program that is executable by a computer, and may be recorded on a computer readable and writable recording medium and be mounted in the management server.

Referring to FIG. 2a, the management server 200 of the present invention may include the display unit 210 which displays leftovers information for each user, a user management unit 220 which registers a user as a meal service recipient and provides nutritional information including one of eating habits and nutritive conditions of registered users, a cafeteria management unit 230 which registers a cafeteria and provides operating information related to the operation of the registered cafeteria, a device control unit 240 which is connected to the first to third scanners to receive acquired scanning data, an image processor 250 which generates leftovers information and ingestion information based on the scanning data received by the device control unit 240, and a database 260 which stores user personal information and the cafeteria operating information.

The display unit 210 may function to display, on a screen thereof, ingestion information for each user generated by the management server 200. A user who has finished a meal may check their ingestion information displayed on the display unit 210 of the management server 200 which is located near the exit after returning a tray and before leaving the cafeteria.

Here, the display unit 210 may be provided separately from other components and may be connected to a main body of the management server 200 located in a separate place to display leftovers information. Alternatively, the display unit 210 of the management server 200 may be omitted, and the user may obtain the above-described leftovers information via their mobile terminal or electronic mail system.

The user management unit 220 may function to manage personal information of a meal service recipient. It is necessary for a user who desires to receive a service from the meal service management system of the present invention to be registered in advance in the management server 200, and the user management unit may determine whether or not the user has been registered as a meal service recipient by comparing the ID card identifying result transmitted from the scanner with the personal information stored in the database.

Further, the user management unit 220 may manage and provide nutritional information related to the eating habits and nutritive conditions of registered users. A description related to the configuration of the user management unit 220 for implementing such a function will be given below.

The cafeteria management unit 230 may function to manage various types of information on the cafeteria at which the meal service management system of the present invention is provided. For example, management of the cafeteria may include generation, updating, deletion, and checking of information on the maximum number of people who can be served at a time at the cafeteria, information on nutritionists belonging to the cafeteria, and information on daily, weekly, and monthly menus. The information may be provided to a system operator.

The device control unit 240 may function to control the scanners connected to the management server 200. The management server 200 may be connected to one or more scanners to receive information related to a user and a tray therefrom, and the device control unit 240 may include a communication module and a controller and may be connected to each scanner via a network to control the scanner and receive required information therefrom.

The image processor 250 may calculate the amount of food served and the amount of leftovers for each user by analyzing pre-meal and post-meal images of a tray received from the scanners using an image processing technique, and may generate ingestion information based the calculated results.

The database 260 may store, for example, personal information and cafeteria information for the implementation of functions provided by the respective components of the management server 200. Further, the database 260 may store various settings for driving the management server 200.

In addition to the major function of providing leftovers information to the user, the management server 200 according to the embodiment of the present invention may further include an advertisement management unit 270 which provides an additional function for generation of profits.

In one example, the advertisement management unit 270 may cause advertisements to be displayed on the display unit 210, or may transmit the advertisements to a user mobile terminal. Here, the advertisements are selected based on the personal information stored in the database 260 and are related to, for example, preferred foods for each person, dietary supplements depending on nutrient intake, medical appliances based on the analysis of eating habits, and restaurants and menus based on personal preference. The function provided by the advertisement management unit 270 is a profit model for an operator of the meal service management system.

As another profit model derived according to the embodiment of the present invention, for example, there may be a so-called "premium service" which provides, for example, a menu management program, ingestion information, nutritional information, the probability of disease, specialized health knowledge, and recipes of side dishes.

Further, the advertisement management unit 270 may have a public service function of providing a message for arousing users to reduce food waste before a meal. In one example, the advertisement management unit may cause a message of informing users who visit the cafeteria of an environmental protection effect achieved when food waste is reduced.

Additionally, a meal cost management unit 280 is provided to differentially charge a meal service recipient for a meal cost according to the amount of food served. In such a procedure of differentially charging a meal cost for each person, the meal cost management unit 280 may adjust a meal cost according to the amount of leftovers and the amount of food served so that different meal costs are charged for each meal service recipient.

To this end, the meal cost management unit 280 may collect information on the amount of food served and the amount of leftovers for each meal service recipient calculated by the image processor 250 to differentially calculate a meal cost, and may accumulate the calculated meal cost in the database 260 to provide a meal cost statement at the time of settlement.

The function of the meal cost management unit 280 described above may be particularly useful when the meal service management system of the present invention is introduced to countries which set a meal cost according to the amount of food served, such as the United States of America and European countries.

The management server 200 according to the embodiment of the present invention may be linked to external systems to provide various types of useful services. To this end, the management server may further include an external system linkage unit 290 which provides various services in cooperation with external systems.

Examples of the services provided in cooperation with external systems may include an insurance service, a user monitoring service, and a medical service.

Figure 2B:
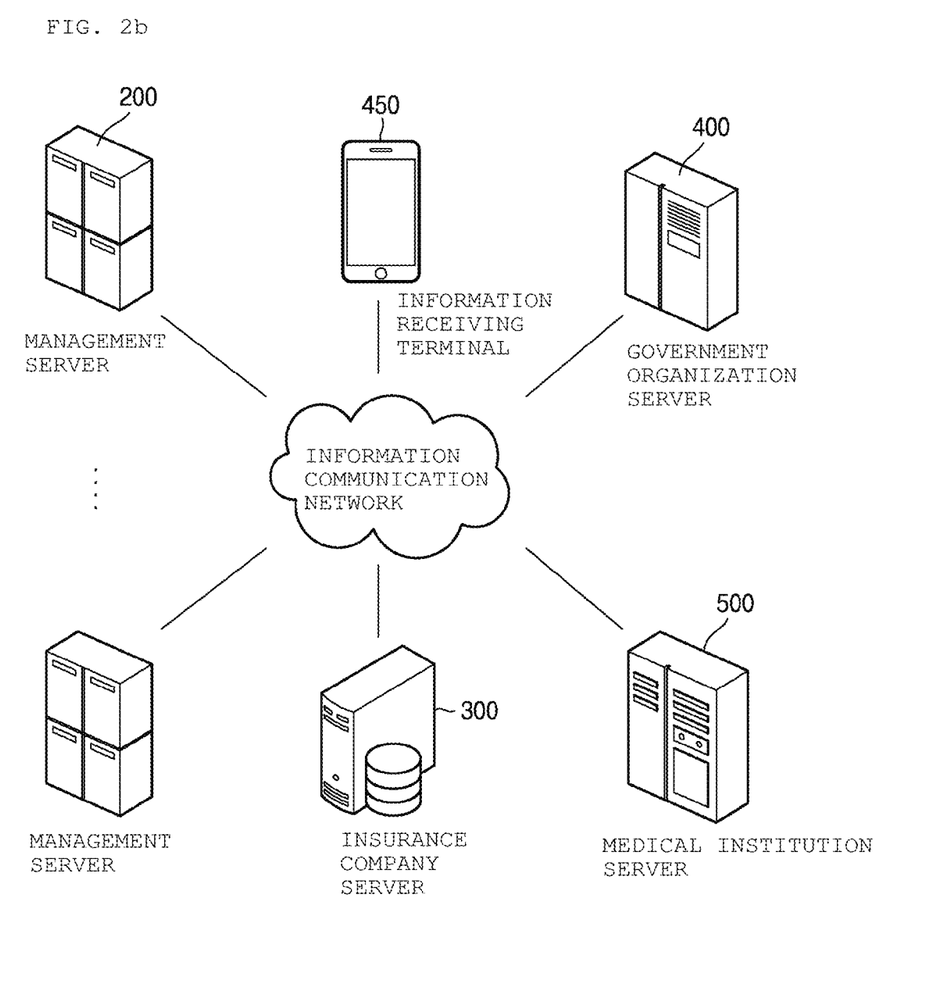
FIG. 2b is a diagram illustrating the linkage structure between external systems and the meal service management system according to the embodiment of the present invention.

FIG. 2b is a diagram illustrating the linkage structure between external systems and the meal service management system according to the embodiment of the present invention. Referring also to FIG. 2b, the management server 200 of the meal service management system according to the embodiment of the present invention may be linked to systems providing various types of services via an information communication network.

The management server 200 of each cafeteria may be linked to an insurance company server 300 and may request an insurance service, such as the discount of an insurance premium when companies, schools, and educational institutions, which manage registered cafeterias, join a group insurance for their members. The management server 200 may provide the insurance company server 300 with ingestion information for each meal service recipient as health care information to present a basis of the discount of an insurance premium, for example, in the case of a term insurance.

Further, the management server 200 may be linked to a government organization server 400 and may provide the government organization server 400 with ingestion information of meal service recipients of the cafeteria. In this way, the government organization server 400 may monitor, for example, the quality of a meal service, the amount of food served, the excessive generation of leftovers, and the provision of an innutritious meal for each cafeteria. Further, the government organization server 400 may provide a service of transmitting pre-meal and post-meal images of a tray, provided from each cafeteria, to an information receiving terminal 450 of a registered person, which may increase the reliability of the quality of food of the cafeteria.

In addition, the management server 200 may be linked to a medical institution server 500 and may provide the medical institution server 500 with ingestion information of meal service recipients of the cafeteria so that the medical institution server 500 may utilize the ingestion information as a reference when making a diagnosis of the meal service recipients. This medical service may expand to a disease prevention service of calculating the probability of disease due to the eating habits of meal service recipients based on the accumulated ingestion information and providing prescription information.

According to the configuration described above, the meal service management system according to the embodiment of the present invention may identify a user of a cafeteria using multiple scanners and may generate and display leftovers information on a screen, thereby allowing the user to easily check their eating habits, such as preferred foods and taste and the average rate and amount of food intake.

Hereinafter, among the components included in the meal service management system according to the embodiment of the present invention, the configurations of the user management unit, the cafeteria management unit, and the image processor, which implement the major functions of the present invention, will be described in more detail with reference to the drawings.

Figure 3A:
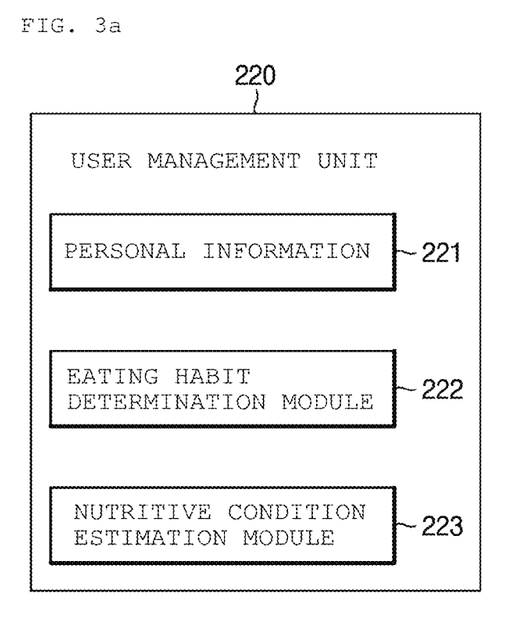
FIGS. 3a and 3b are diagrams illustrating the configurations of a user management unit and a cafeteria management unit constituting the management server of the meal service management system according to the embodiment of the present invention.
Figure 3B:
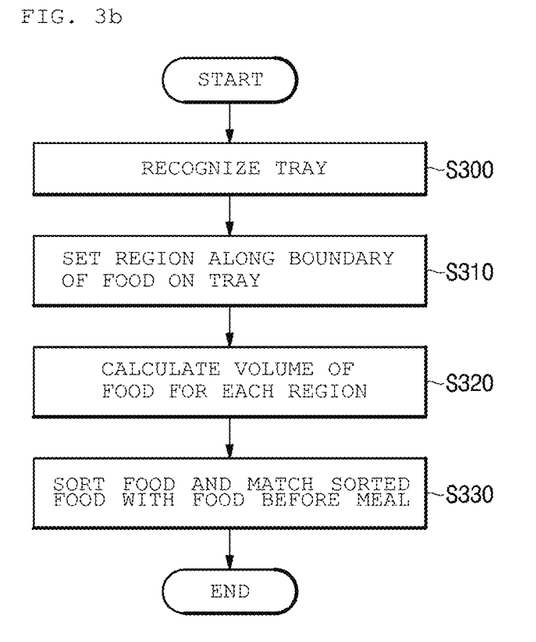
Figure 4:
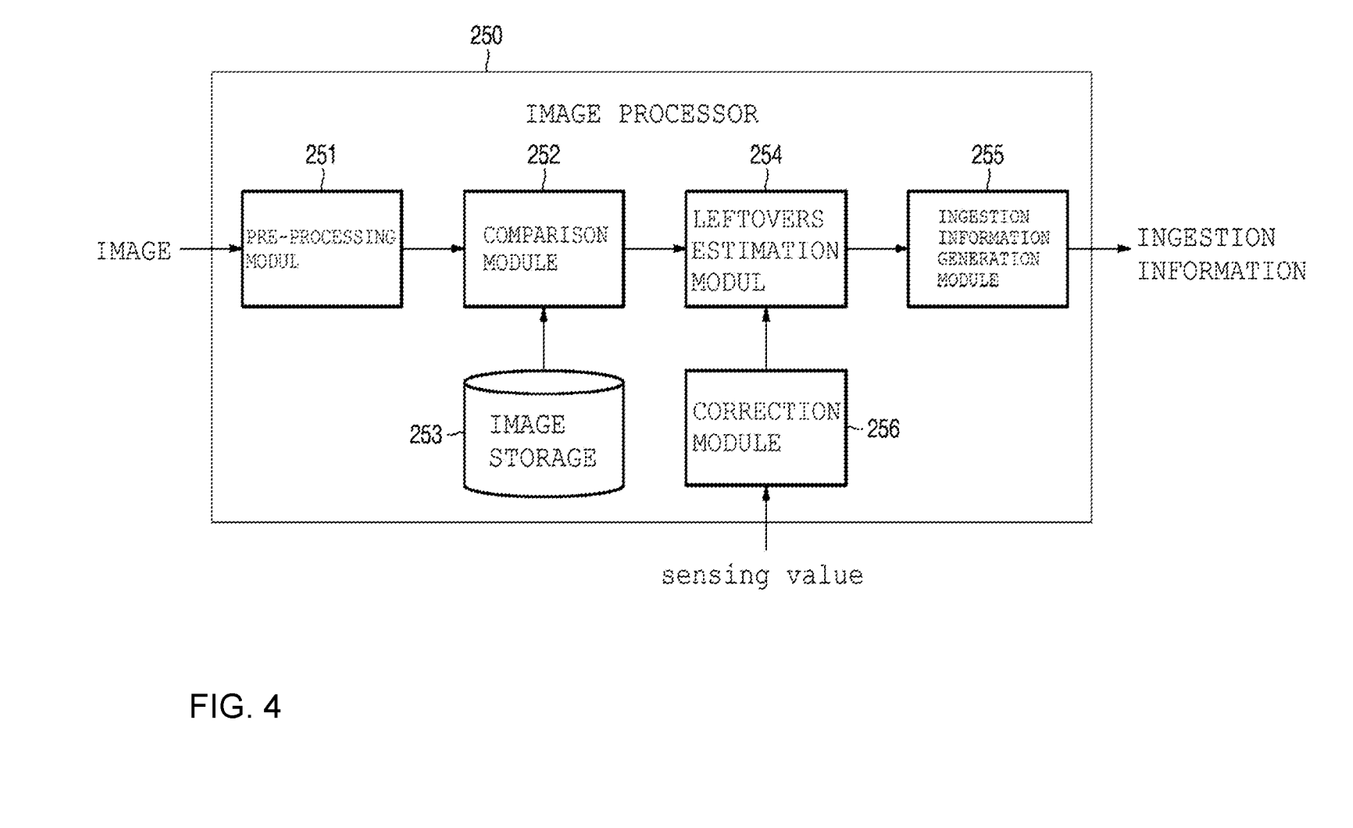
FIG. 4 is a diagram illustrating the configuration of an image processor among components of the management server of the meal service management system according to the embodiment of the present invention.

FIGS. 3a and 3b are diagrams illustrating the configurations of the user management unit and the cafeteria management unit constituting the management server of the meal service management system according to the embodiment of the present invention, and FIG. 4 is a diagram illustrating the configuration of the image processor among the components of the management server of the meal service management system according to the embodiment of the present invention.

First, referring to FIG. 3a, the user management unit 220 of the management server of the present invention may be composed of one or more functional modules. These modules may include a personal information processing module 221 which determines whether or not a user limited to a meal service recipient is registered with the system by using an ID card issued in advance to the user, or manages personal information of registered users, an eating habit determination module 222 which determines individual eating habits with reference to various types of information, and a nutritive condition estimation module 223 which calculates the current nutritive condition for each user.

The personal information processing module 221 may function to manage personal information of users registered in the meal service management system of the present invention. A system operator may input, for example, the name, phone number, and address of a meal service recipient to the personal information processing module to generate a user account, and the personal information processing module may generate and store personal information for each user account. The personal information is related to, for example, eating habits, preferred foods, food allergies and current nutritive conditions of users.

The eating habit determination module 222 may determine the eating habits of each user based on details of meals served to the user and may store determined information. Whenever the user has a meal at the cafeteria, the eating habit determination module 222 determines the eating habits of the user using information on details of meals served to the user including the kinds of food served, the rate and amount of food intake, and the amount of leftovers. The determined result of eating habits may be applied to the personal information.

The nutritive condition estimation module 223 may estimate the current nutritive condition of each user based on details of meals served to the user, and may store the estimated result as nutritional information. The nutritive condition estimation module 223 may calculate the kinds of food ingested by the user and the amount of food intake based on the user history of using the cafeteria within a predetermined duration and leftovers information created when the user uses the cafeteria, and may generate nutritional information by analyzing the current nutritive condition of the user based on the calculated information. The nutritional information may be applied to the personal information, like the eating habit information.

Referring to FIG. 3b, the cafeteria management unit 230 of the management server of the present invention may include one or more modules. These modules may include a cafeteria management module 231 which manages information on the cafeteria where the system of the present invention is provided, a food material examination module 232 which performs procedures related to the examination of food materials supplied to the cafeteria, and a menu generation module 233 which generates and provides weekly menu schedule information.

The cafeteria management module 231 may function to manage information on the cafeteria where the meal service management system of the present invention is provided, and may generate, update, and delete information on the maximum number of people who can be served at a time at the cafeteria and nutritionists belonging to the cafeteria.

The food material examination module 232 may function to examine food materials supplied to the cafeteria. The food materials may be supplied every day to the cafeteria, and the nutritionists belonging to the cafeteria may input all procedures of receiving, examining, and storing the food materials to the management server to check the same later. Thus, the function of the food material examination module 232 may be limitedly executed only by a nutritionist authority account.

The menu generation module 233 may function to allow nutritionists registered in the system to generate a menu list related to food served at the cafeteria. The nutritionists may make a weekly menu in consideration of the nutritive conditions of meal service recipients at the beginning of each month, and may generate menu information by inputting the menu via a UI provided by the menu generation module 233. The menu information is posted every week on the management server 200 and the website connected thereto, for example.

It is to be noted that the meal service management system according to the embodiment of the present invention may identify a meal service recipient by scanning a user ID card via one or more scanners provided at the cafeteria, may acquire the amount of food served and the amount of leftovers by scanning a tray before and after a meal, and may generate leftovers information based on an acquired results.

In particular, in the embodiment of the present invention, ingestion information with higher accuracy may be provided by applying an image processing technique to images acquired via the scanners, and the management server may include the image processor for applying the image processing technique.

Referring to FIG. 4, the image processor 250 included in the management server of the present invention may include a pre-processing module 251 which pre-processes a post-meal image obtained by photographing a tray after a meal, a comparison module 252 which compares the post-meal image with a pre-meal image received from an image storage 253, a leftovers estimation module 254 which generates leftovers information based on the comparison result of the comparison module 252, and an ingestion information generation module 255 which generates and outputs ingestion information, corresponding to the leftovers information, as a numerical value, text, or a graph.

The pre-processing module 251 may perform a pre-processing, such as a change in size and noise removal for comparison, on the pre-meal and post-meal images of the tray transmitted from the scanners. The pre-meal image for each identified tray may be stored in the image storage and may then be provided to the comparison module 252 after the pre-processing when the post-meal image is input.

The comparison module 252 may quantify the pre-processed pre-meal and post-meal images for comparison. These images may consist of multiple pixels having gray values, and the comparison module 252 may perform comparison by calculating the difference between the pixel gray values.

The image storage 253 may store the pre-processed pre-meal image for each tray, and may provide the pre-meal image corresponding to the post-meal image in response to a request of the comparison module 252.

The images stored in the image storage 253 may be automatically deleted after a comparison procedure is performed or after a certain time has passed.

The leftovers estimation module 254 may determine the amount of food served and the amount of leftovers from the pre-meal image and the post-meal image, and may calculate leftovers information from the difference therebetween. In an image input from the scanner, a gray or white region connected to each edge of the image may be determined as corresponding to the tray, and the comparison module may calculate leftovers information based on an increase in the area of the gray or white region of the post-meal image compared to the pre-meal image.

Further, the leftovers estimation module 254 may estimate a reduction in the volume of food, such as steamed rice and side dishes, and a reduction in the depth of soup based on the pre-meal and post-meal images, or may make two histograms indicating the distribution of brightness of the entire pre-meal image and the entire post-meal image to calculate a change in the amount of food according to the difference between the two histograms.

The ingestion information generation module 255 may generate ingestion information as a numerical value, text, or a graph according to the leftovers information calculated by the leftovers estimation module 254. The ingestion information may be applied to the personal information, and may be displayed on the screen of the display unit of the management server, or may be transmitted to a user terminal via a network.

The image processor 250 according to the embodiment of the present invention may further include a correction module for increasing the accuracy of estimating a change in the amount of food.

The correction module 256 may receive a sensing value from at least one sensor provided in each scanner, and may correct leftovers information by applying the sensing value to a change in the amount of food, calculated by the leftovers estimation module 254, at a predetermined ratio.

Specifically, the scanner may be equipped with a temperature sensor or a weight sensor such as a load cell, and the correction module 256 may generate a correction value using the sensed temperature or weight of a tray to correct leftovers information.

In one example, when the difference between the temperatures of the tray before and after a meal is not large, it may be determined that food, in particular, soup is hardly consumed. In another example, when the difference between the weights of the tray before and after a meal is not large, it may be determined that the amount of food intake is very small.

With regard to identification of the kinds of food such as soup, steamed rice, and side dishes, kimchi may be excluded from the determination criterion since the temperature of kimchi commonly does not exceed 30° C., or the determination criterion of soup may be corrected such that soup of 40° C. or less is excluded.

The correction module 256 may generate the correction value as various numbers of cases are set with respect to sensing values provided from sensors.

According to the configuration described above, the management server according to the embodiment of the present invention may manage both a meal service recipient and a cafeteria, and may provide the meal service recipient with ingestion information based on the amount of leftovers and the amount of food intake and their nutritional information, for example.

Hereinafter, an operating method of the meal service management system according to an embodiment of the present invention will be described with reference to the drawings.

Figure 5:
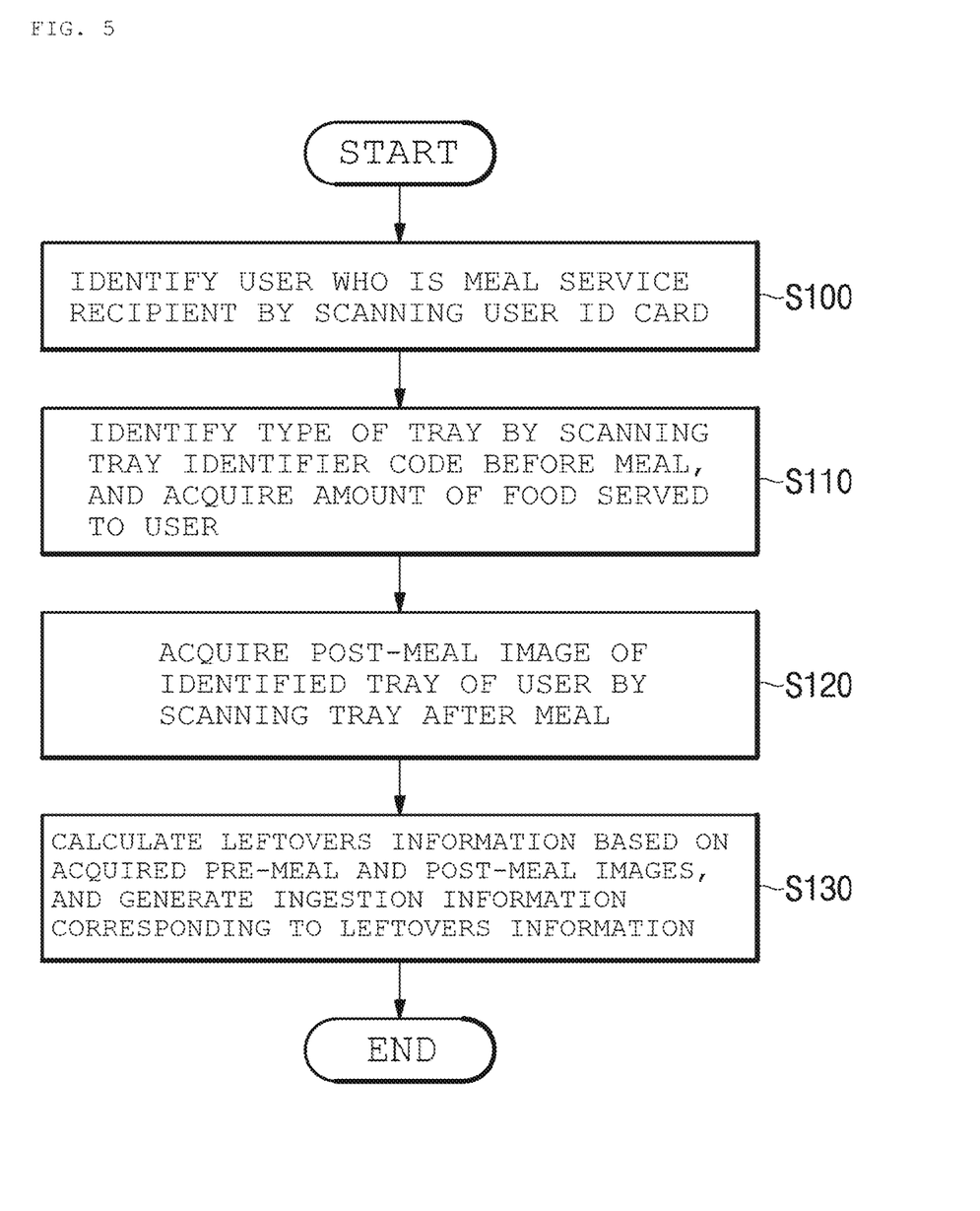
FIG. 5 is a flowchart illustrating an operating method of the meal service management system according to the embodiment of the present invention.

FIG. 5 is a flowchart illustrating an operating method of the meal service management system according to the embodiment of the present invention. In the following description, the subject for each step is the multiple scanners, the management server, and the components of the management server, which constitute the meal service management system of the present invention described above even if not stated.

Referring to FIG. 5, the operating method according to the embodiment of the present invention is for the meal service management system including the first to third scanners and the management server, and may include a step S100 of identifying a user who is a meal service recipient by scanning a user ID card, a step S110 of identifying a tray before a meal by scanning a tray identifier code and acquiring a pre-meal image of the tray of the user, a step S120 of acquiring a post-meal image of the identified tray of the user by scanning the tray after the meal, and a step S130 of calculating leftovers information based on an acquired pre-meal and post-meal images and generating ingestion information corresponding to the leftovers information.

In step S100 of identifying a user who is a meal service recipient by scanning a user ID card, the first scanner provided at the cafeteria scans the ID card presented by the user and transmits scanning information to the management server, and the management server identifies that the user of the ID card is a meal service recipient.

Subsequently, in step S110 of identifying a tray before a meal by scanning a tray identifier code and acquiring a pre-meal image of the tray of the user, when a normal user, i.e., the user identified as a meal service recipient picks up a tray and puts food on the tray, the second scanner scans a tray identifier code and simultaneously, scans the food on the tray to generate a pre-meal image of the tray before a meal and transmits the pre-meal image to the management server, and subsequently, the management server identifies the tray based on the result of scanning the identifier code and acquires the pre-meal image. Here, the pre-meal image may be processed by the image processor of the management server so as to be used to calculate the amount of food served.

In step S120 of acquiring a post-meal image of the identified tray of the user by scanning the tray after the meal, the image processor of the management server acquires a post-meal image for each tray that is an image of the tray after the meal. The post-meal image may be used to calculate the amount of leftovers.

Thereafter, in step S130 of calculating leftovers information based on an acquired pre-meal and post-meal images and generating ingestion information corresponding to the leftovers information, leftovers information and ingestion information, which correspond to the actual amount of food intake, are generated using the difference between the amount of food served and the amount of leftovers calculated in steps S110 and S120.

In particular, in step S130, it can be appreciated that the leftovers information indicates the actual amount of food ingested by the user since the image processor calculates the leftovers information based on the difference between the amount of food served and the amount of leftovers. In the present invention, by generating the ingestion information on the amount of food ingested by the user based on leftovers information, and outputting the ingestion information as a numerical value, text, or a graph, for example, useful ingestion information for the user may be provided.

Although not illustrated, after step S130, the method may further include a step of displaying the ingestion information per meal and a step of outputting a coupon according to the ingestion information. According to these steps, the accurate amount of food ingested by the user may be determined based on the ingestion information, and by providing the user with the ingestion information on the amount of food intake, information on calories and nutrients of food may further be provided. In addition, a variety of rewards for the effort of reducing leftovers, for example, a coffee coupon may be provided.

That is, according to the embodiment of the present invention, by providing a meal service provider with accurate and specific information on user's preferred foods and the amount of food intake, information helpful to improve the quality of a meal service and reduce leftovers may be provided.

With the steps described above, the operating method of the meal service management system according to the embodiment of the present invention may provide ingestion information depending on the actual amount of food intake for each meal service recipient based on an acquired pre-meal and post-meal images of the tray, thereby allowing the user to manage their eating habits by checking the ingestion information.

Hereinafter, a method of generating leftovers information before and after a meal in the meal service management system according to the embodiment of the present invention will be described in detail. In the following steps, the execution subject is the image processor and the comparison module thereof even if not stated.

Figure 6A:
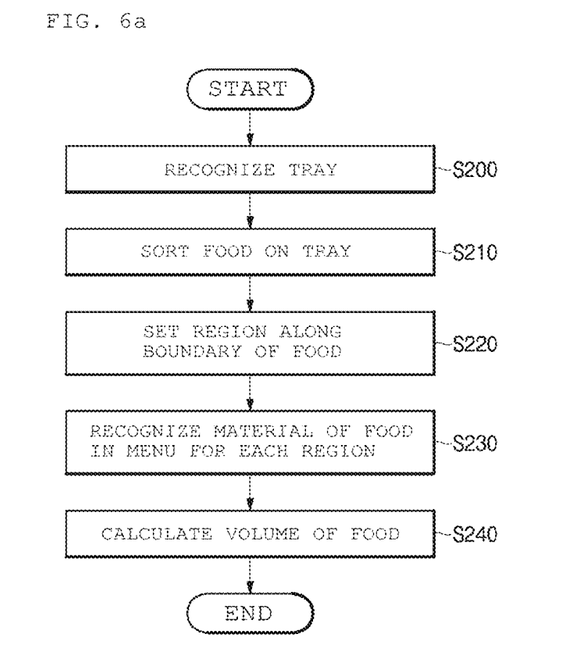
FIGS. 6a and 6b are flowcharts illustrating an image analysis method for generating leftovers information in the meal service management system according to the embodiment of the present invention.
Figure 6B:
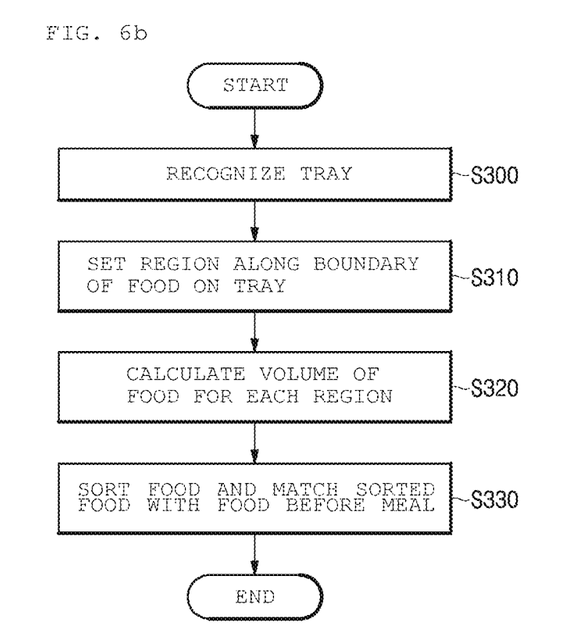

FIGS. 6a and 6b are flowcharts illustrating an image analysis method for generating leftovers information in the meal service management system according to the embodiment of the present invention.

First, referring to FIG. 6a, in step S200 of recognizing a tray, the comparison module of the image processor recognizes a tray photographed by the scanner, on which all foods have been completely received. Specifically, the comparison module divides respective sections of the tray in which different foods such as steamed rice, soup, and side dishes, and a bowl are received by partition lines formed on the tray, and recognizes the orientation of the tray to determine the sections in which the foods are received.

Subsequently, in step S210 of sorting the foods on the tray, the comparison module recognizes the kind of food for each section divided in the tray. By comparing a food image acquired by an image sensor, i.e., the scanner with multiple food-related learning images accumulated in a knowledge database for machine learning, the comparison module determines the kind of food based on the result of matching the image recognition result for each section with a menu of the day.

In this case, when the success rate of matching exceeds 80%, the result is immediately stored in the image storage. When the success rate of matching is 80% or less, the food is sorted as undefined food and then, the result is stored in the image storage.

In step S220 of setting a region along the boundary of food, the boundary of food is accurately set for each section. Here, for example, the temperature, color, and shape of food may be considered. For example, the boundary of food, which accurately separates salad and kimchi from each other, among the foods on the tray may be set.

Subsequently, in step S230 of recognizing food materials for each region according to a menu, food materials in the region defined by the boundary of food are recognized as the boundary of food is set in the state in which a menu for each section is recognized.

In one example, assuming that a tray is divided into first to fifth sections and salad is received in the first section, materials of the salad in the first section, i.e., a cabbage, broccoli, cucumber, and carrot are recognized respectively. Even in step S230, machine learning image comparison may be performed. In this case, even if it is assumed that the same amount of salad is received in the first section, the amount of recognized materials may be different for each tray.

Subsequently, in step S240 of calculating the volume of food, the volume of each food is recognized on the basis of the boundary of food using information acquired via a 3D sensor included in the scanner. The 3D sensor may measure the depth of an object. As such, the amount of food may be calculated by measuring the height of food inside the boundary of food and calculating the volume of food using the boundary and the height.

According to the steps described above, the image processor may generate leftovers information by storing an acquired pre-meal image and then using the post-meal image obtained by again photographing the tray after a meal.

Referring to FIG. 6b, in step S300 of recognizing a tray, the comparison module of the image processor recognizes a tray photographed by the scanner, on which all foods have been completely received, and defines sections along partition lines on the tray.

In step S310 of setting a region along the boundary of food on the tray, the boundary of food is accurately set for each section.

Subsequently, in step S320 of calculating the volume of food for each region, the volume of each food on the basis of the boundary of food is recognized according to information acquired using a 3D sensor included in the scanner. In step S320, upon determining that the volume of food in a section is 5% or less compared to that of a pre-meal image, the comparison module regards that the amount of leftovers in the corresponding section is 0% and thus, proceeds to the process of calculating the volume of food in other sections. Then, upon determining that the volume of food in any other section exceeds 5%, the comparison module performs the following step S330.

In step S330 of sorting the foods and matching the sorted foods with foods before a meal, materials of food included in a menu are recognized using machine learning images of a knowledge database, and the amount of leftovers for each menu or for each material is calculated based on the volume calculated in steps S310 and S320 to generate leftovers information.

Meanwhile, in order to generate ingestion information in the operating method of the meal service management system described above, for example, the amount of food served and the amount of leftovers are acquired by scanning the tray before and after a meal. Hereinafter, the structure of the scanner used in the meal service management system according to an embodiment of the present invention will be described.

Figure 7:
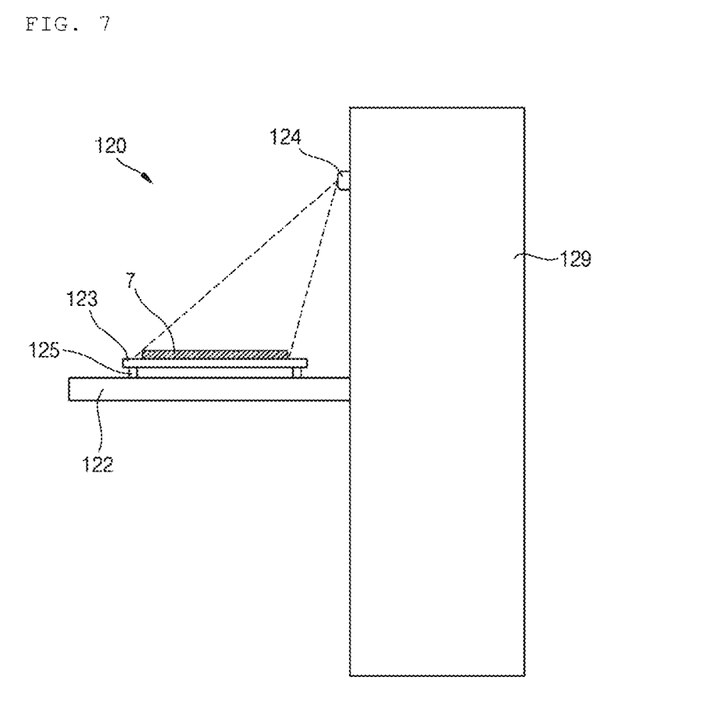
FIG. 7 is a diagram illustrating the structure of a scanner used in the meal service management system according to the embodiment of the present invention.

FIG. 7 is a diagram illustrating the structure of a scanner used in the meal service management system according to an embodiment of the present invention.

Referring to FIG. 7, the scanner 120 according to the embodiment of the present invention may include a body 121, a support 122 connected perpendicularly to one side of the body 121, a cradle 123 coupled to the top of the support 122 so that a tray is seated thereon, and a stereo camera 124 provided on one side of the body 121 to face the top of the cradle 123 and configured to photograph food on the tray 7.

The body 121 may define the external appearance of the scanner 120 and may be fixed near the pick-up counter of the cafeteria. The support 122 may be connected to one side of the body 121 at a predetermined height.

The support 122 may protrude laterally to have a predetermined length, and may have a rectangular shape when viewing from above. The support 122 supports the cradle 123 placed thereon from below.

The tray before and after a meal may be seated on the cradle 123. The cradle 123 may be fixedly coupled to the support 122 so that the tray faces a lens of the stereo camera 124 which will be described below.

In particular, the bottom of the cradle 123 may be supported by and coupled to at least one load cell 125 provided on the support 122. The load cell 125 may sense the weights of the cradle 123 and the tray 7 seated on the cradle and may transmit the sensed weights to the management server.

Additionally, at least one temperature sensor (not illustrated) that senses the temperature of the tray seated on the cradle 123 may be mounted on one side of the cradle. The temperature sensed by the temperature sensor may be transmitted to the management server. As such, the management server may use the currently measured weight and temperature of food on the tray as a correction value for calculating the amount of food served, the amount of leftovers, or a change in the amount of food.

The stereo camera 124 may be provided on the body 121 so as to be spaced apart from the support 122 by a predetermined distance. Thereby, the stereo camera 124 may be positioned so as to be able to scan the entire region of the tray 7 on the cradle 123.

The stereo camera 124 is oriented such that the lens thereof faces the cradle 123, and photographs images of the tray before and after a meal to transmit the images to the management server.

Although many details have specifically been described in the above description, these should be construed as exemplifying preferred embodiments rather than limiting the scope of the invention. Thus, the invention should not be defined by the described embodiments, but should be defined by the claims and equivalents thereto.

The invention claimed is:

1. A meal service management system comprising:
   a first scanner configured to scan a tray to acquire a pre-meal image of the tray before a meal provided to the user;
   a second scanner configured to scan the tray to acquire a post-meal image of the tray after the meal provided to the user; and
   a management server configured to generate ingestion information of the user based on the acquired pre-meal and post-meal images,
   wherein each of the first and second scanners includes:
      a body;
      a support connected perpendicularly to one side of the body;
      a cradle coupled to a top of the support, the tray being seated on the cradle; and
      a camera provided on the one side of the body so as to face a top of the cradle and configured to photograph food on the tray.

2. The system according to claim 1, wherein the management server includes:
   a user management unit configured to register a user as a meal service recipient, and provide nutritional information including one of eating habits and nutritive conditions of registered users;
   a cafeteria management unit configured to register a cafeteria, and provide operating information related to an operation of the registered cafeteria;
   a device control unit connected to the first and second scanners to receive acquired scanning data;
   an image processor configured to generate the ingestion information based on the scanning data received by the device control unit; and
   a database configured to store personal information of the user and the operating information of the cafeteria.

3. The system according to claim 2, wherein the user management unit includes:
   a personal information processing module configured to generate, update, or delete the personal information of the user;
   an eating habit determination module configured to determine an eating habit of the user based on ingestion information for a predetermined duration and apply the eating habit to the nutritional information; and
   a nutritive condition estimation module configured to estimate a current nutritive condition of the user according to the nutritional information.

4. The system according to claim 2, wherein the cafeteria management unit includes:
   a cafeteria management module configured to generate, update, or delete the operating information;
   a food material examination module configured to generate examination information based on an examination result of a nutritionist with respect to a plurality of food materials supplied to the cafeteria; and
   a menu generation module configured to generate a menu list in response to an input of the nutritionist.

5. The system according to claim 2, wherein the image processor includes:
   a pre-processing module configured to pre-process the post-meal image obtained by photographing the tray after the meal;
   a comparison module configured to compare the post-meal image with the pre-meal image received from an image storage;
   a leftovers estimation module configured to generate leftovers information based on a comparison result of the comparison module; and
   an ingestion information generation module configured to generate the ingestion information corresponding to the leftovers information and output the ingestion information as a numerical value, text, or a graph.

6. The system according to claim 5, wherein the second scanner is connected to at least one sensor, and wherein the image processor further includes a correction module configured to receive a sensing value from the sensor and generate a correction value for correction of the leftovers information based on the sensing value.

7. The system according to claim 2, wherein the management server includes an advertisement management unit configured to provide advertisement information for a medical appliance or food customized for each user, recommended menu information, or other additional information with reference to the nutritional information.

8. The system according to claim 1, wherein a bottom of the cradle is supported by and coupled to at least one load cell provided on the support.

9. The system according to claim 1, wherein the cradle is equipped with at least one temperature sensor that senses a temperature of the tray seated on the top of the cradle.

10. The system according to claim 2, wherein the management server includes a meal cost management unit configured to differentially calculate a meal cost for an amount of food per person depending on ingestion information for each user.

11. The system according to claim 2, wherein the management server includes an external system linkage unit linked to at least one external system that provides an insurance service, a user monitoring service, or a medical service via an information communication network.

\* \* \* \* \*